US011844623B1

(12) United States Patent
Bosworth et al.

(10) Patent No.: US 11,844,623 B1
(45) Date of Patent: Dec. 19, 2023

(54) SYSTEMS AND METHODS FOR TRACKING SLEEP

(71) Applicant: META PLATFORMS TECHNOLOGIES, LLC, Menlo Park, CA (US)

(72) Inventors: Andrew Garrod Bosworth, San Mateo, CA (US); Charles Liam Goudge, Menlo Park, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 431 days.

(21) Appl. No.: 17/142,592

(22) Filed: Jan. 6, 2021

(51) Int. Cl.
*A61B 5/00* (2006.01)
*A61B 5/0205* (2006.01)
*A61B 5/024* (2006.01)
*A61B 5/08* (2006.01)
*A61B 5/11* (2006.01)

(52) U.S. Cl.
CPC .......... *A61B 5/4815* (2013.01); *A61B 5/0035* (2013.01); *A61B 5/0205* (2013.01); *A61B 5/0075* (2013.01); *A61B 5/0077* (2013.01); *A61B 5/02438* (2013.01); *A61B 5/08* (2013.01); *A61B 5/11* (2013.01); *A61B 5/6803* (2013.01); *A61B 2560/0456* (2013.01); *A61B 2562/0219* (2013.01)

(58) Field of Classification Search
CPC ... A61B 5/4815; A61B 5/0035; A61B 5/0205; A61B 5/0075; A61B 5/0077; A61B 5/02438; A61B 5/08; A61B 5/11; A61B 5/6803; A61B 2560/0456; A61B 2562/0219
See application file for complete search history.

(56) References Cited

U.S. PATENT DOCUMENTS

| | | | |
|---|---|---|---|
| 9,252,605 B1 * | 2/2016 | Custon | H02J 7/0042 |
| 10,368,799 B2 | 8/2019 | Sannholm et al. | |
| 10,568,565 B1 * | 2/2020 | Kahn | A61B 5/1126 |
| 10,610,133 B2 | 4/2020 | Rabb et al. | |

(Continued)

OTHER PUBLICATIONS

"Details—SAMi: The Sleep Activity Monitor", URL: https://www.samialert.com/details, as accessed on Dec. 17, 2020, 7 pages.

(Continued)

*Primary Examiner* — Eric F Winakur
*Assistant Examiner* — Jonathan Drew Moroneso
(74) *Attorney, Agent, or Firm* — Greenberg Traurig, LLP

(57) ABSTRACT

An apparatus for sleep tracking may include (i) a sensor that detects whether a wearable device is being worn by a user, (ii) a mode-switching module that switches the wearable device between an active mode when the sensor detects that the wearable device is being worn by the user and a sleep-tracking mode when the sensor detects that the wearable device is not being worn by the user, (iii) a detector that, when the wearable device is in the sleep-tracking mode, detects signals associated with sleep behavior of the user, and (iv) a sleep-tracking module that, when the wearable device is in the sleep-tracking mode, monitors the user's sleep based at least in part on an evaluation of the signals associated with the sleep behavior of the user. Various other methods, systems, and computer-readable media are also disclosed.

19 Claims, 11 Drawing Sheets

(56) References Cited

U.S. PATENT DOCUMENTS

| | | | |
|---|---|---|---|
| 2016/0218553 A1* | 7/2016 | He | H02J 7/0044 |
| 2016/0345832 A1 | 12/2016 | Pavagada Nagaraja et al. | |
| 2018/0070840 A1* | 3/2018 | Cronin | A61B 5/7435 |
| 2018/0214028 A1* | 8/2018 | Zhang | A61B 5/4318 |
| 2019/0015045 A1* | 1/2019 | Li | G04C 3/002 |
| 2021/0142894 A1* | 5/2021 | Räisänen | A61B 5/02444 |
| 2022/0015648 A1* | 1/2022 | Zinner | H04R 1/028 |

OTHER PUBLICATIONS

Casaccia et al., "Experimental Assessment of Sleep-Related Parameters by Passive Infrared Sensors: Measurement Setup, Feature Extraction, and Uncertainty Analysis", Sensors (Basel), MDPI, vol. 17, No. 3773, Aug. 31, 2019, 21 pages.

"ONE Dock Duo Power Station Dock", URL: https://www.amazon.com/CERTIFIED-Station-Charger-Built-ORIGINAL/dp/B01EKLWUFM, as accessed on Dec. 23, 2020, pp. 1-11.

"Life With Oura", URL: https://ouraring.com/life-with-oura, as accessed on Dec. 17, 2020, 21 pages.

"Beddit Sleep Monitor", URL: https://www.beddit.com/, as accessed on Dec. 17, 2020, 13 pages.

Chen et al., "Sleep monitoring using an infrared thermal array sensor", Proc. SPIE 10970, Sensors and Smart Structures Technologies for Civil, Mechanical, and Aerospace Systems, 109701D, Mar. 27, 2019, 12 pages.

\* cited by examiner

SYSTEMS AND METHODS FOR TRACKING SLEEP

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
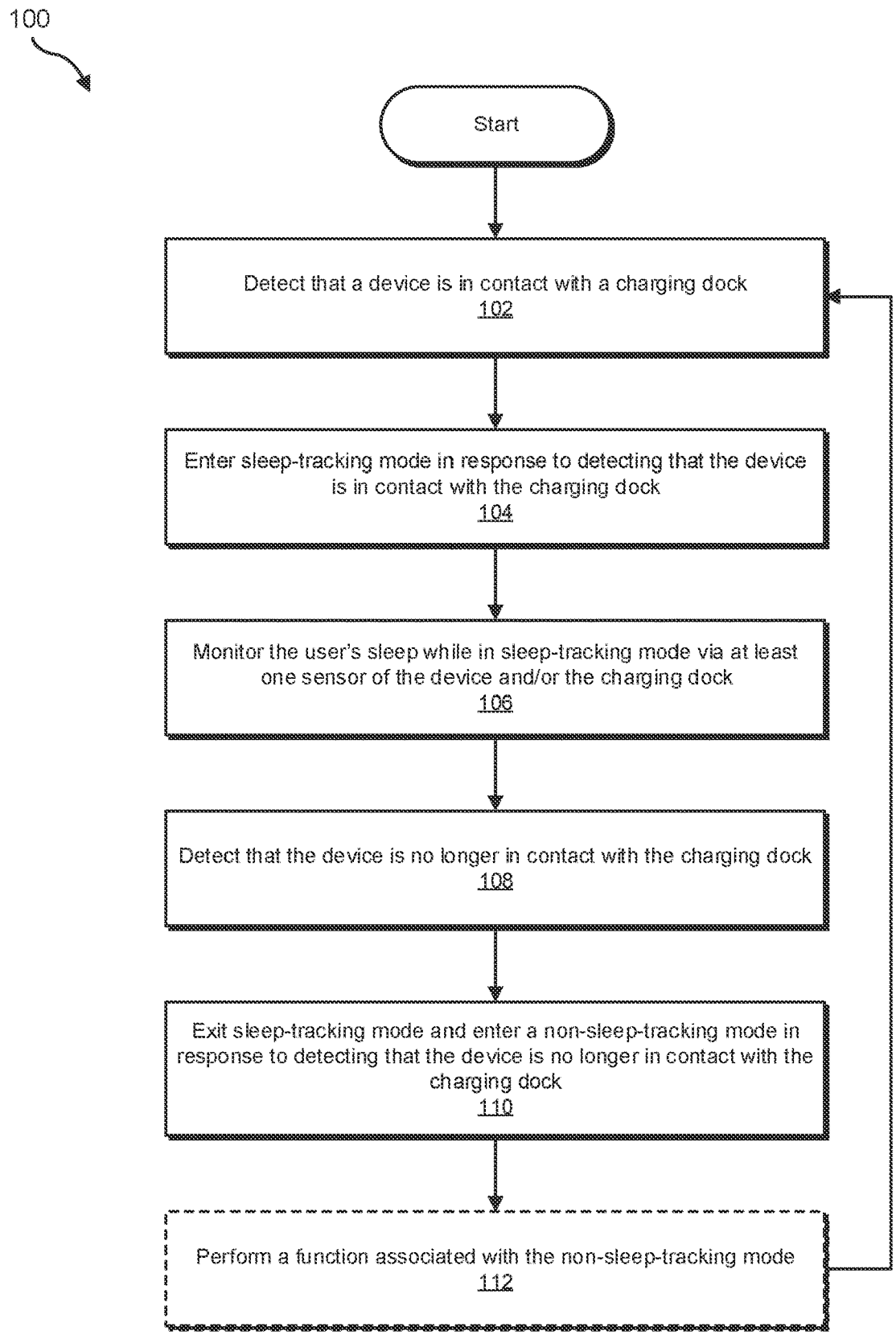
FIG. 1 is a flow diagram of an exemplary method for tracking sleep.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

Features from any of the embodiments described herein may be used in combination with one another in accordance with the general principles described herein. These and other embodiments, features, and advantages will be more fully understood upon reading the following detailed description in conjunction with the accompanying drawings and claims.

DETAILED DESCRIPTION OF EXEMPLARY EMBODIMENTS

The present disclosure is generally directed to systems and methods for performing non-intrusive sleep tracking using devices that are primarily designed to perform non-sleep-tracking functions. In many cases, wearable devices designed for monitoring sleep are uncomfortable or intrusive to wear while sleeping, potentially interfering with the user's sleep and defeating the purpose of the device. As will be explained in greater detail below, however, sensors on multi-purpose portable or wearable devices may be repurposed to non-intrusively monitor the user's sleep while the device is not being worn, such as when the device is placed on the user's nightstand (e.g., while charging overnight). For example, an emitter (such as an infrared (IR) emitter) and corresponding sensor of a wearable device may be used to monitor the user's movement during sleep when the device is not being worn. Similarly, a microphone on the device may be used to monitor a user's breathing. In some examples, the wearable device may detect whether it is being worn and may automatically transition between a wearable mode and a sleep-tracking mode, further increasing convenience for the user.

Additionally or alternatively, a charging dock on or near a bed may be designed to facilitate non-intrusive sleep tracking, either on its own or in combination with wearable and/or portable devices. For example, the charging dock may be shaped to hold a wearable device such that relevant emitters, detectors, and/or other sensors of the wearable device are pointed towards the sleeping user when the wearable device is charging. Such an arrangement may enable the wearable device to track the user's movement during sleep by emitting radiation (such as IR light) toward, and detecting radiation reflected from, the user, all while the wearable device is charging in the charging dock. In another example, the charging dock may itself emit and/or detect radiation (e.g., IR light) to track the user's movement during sleep.

In an additional example, the charging dock may be mounted or directly attached to a portion of the bed itself (e.g., the headboard). In this example, the charging dock may include a pouch or other housing designed to hold a wearable or mobile device (such as a smartwatch or smartphone) in place while charging. Such an arrangement may enable the device within the pouch to monitor, using one or more sensors, various aspects of the user's sleep while charging, including the user's movement (based on, e.g., vibrations generated by the user during sleep), respiratory rate (using, e.g., a microphone), and heart rate, as explained in greater detail below. In some examples, the systems described herein may also monitor additional conditions of the room, such as the temperature, ambient noise level, and/or light level, to provide a more complete picture of the user's sleep.

By repurposing existing classes of devices (e.g., wearable devices, mobile devices, and/or chargers) to monitor and evaluate user sleep behavior, the systems described herein may conveniently collect sleep data, providing sleep tracking information for users who otherwise have no access to such data and/or enhancing data collection for users who are also using specialized sleep-tracking devices. In addition, because the sleep-tracking approaches described herein are non-intrusive, the disclosed systems may potentially capture more accurate and/or reliable sleep information, potentially resulting in a more complete picture of a user's sleep without interfering with their comfort or rest.

FIG. 1 is a high-level flow diagram of an exemplary method 100 for sleep tracking. In some examples, at step 102, the systems described herein may detect that a device is in contact with a charging dock. For example, and as will be described in greater detail below in connection with FIGS. 2-5, the systems described herein may detect that a mobile device (e.g., a smart phone, tablet, etc.) and/or a wearable device is in contact with a charging dock.

The term "wearable device" may generally refer to any item of clothing and/or accessory that is configured to be worn on the body and that performs at least one computing function. In some embodiments, a wearable device may include a housing dimensioned to be physically worn by the user. For example, a smart watch may include a watch band dimensioned to fit around a user's wrist. In some examples, a wearable device may be configured to interface with multiple different housings in order to be worn in different ways, such as a wearable device that may be attached to a watch band, a helmet mount, a backpack, a bike mount, and/or a necklace. In some embodiments, a wearable device may perform multiple functions, while in other embodiments a wearable device may be primarily designed for a single function. For example, a smart watch may display message notifications, record audio notes, track biometric data (e.g., heart rate), and/or display the time, while a set of augmented reality glasses may interface with an augmented reality system but may not be designed to provide non-augmented-reality functions. Examples of wearable devices may include, without limitation, smart watches, rings, necklaces, belts, glasses, headbands, headwear, clothing, backpacks, and/or other packs.

The term "charging dock" or "charger" may generally refer to any device designed to provide electric charge to one or more other devices. In some embodiments, a charging dock may provide charge via wireless power transfer such as inductive charging. Additionally or alternatively, a charging dock may have one or more cords, adapters, ports, terminals, and/or plugs to provide charge via wired charging. In some examples, when a chargeable device is in contact with a charging dock, the chargeable device may be physically touching the charging dock (e.g., resting on top of the charging dock, within a pouch or housing formed by the charging dock, etc.). Additionally or alternatively, a chargeable device in contact with a charging dock may be plugged into the charging dock via a cord.

In some embodiments, at step 104, the device and/or charging dock may enter sleep-tracking mode in response to detecting that the device is in contact with the charging dock. In some examples, at step 106, the device and/or charging dock may then monitor the user's sleep while in sleep-tracking mode via at least one sensor of the device and/or the charging dock. At some later point, at step 108, the device and/or charging dock may detect that the device is no longer in contact with the charging dock. At step 110, the device and/or charging dock may exit sleep-tracking mode and enter a non-sleep-tracking mode in response to detecting that the device is no longer in contact with the charging dock. Specifically, at step 112, the device may perform a function associated with the non-sleep-tracking mode. For example, the device may record video, send and/or receive messages, and/or perform any of a variety of other computing functions not related to sleep tracking.

The systems described herein may function in any of a variety of configurations. In some embodiments, the systems described herein may be hosted entirely on a wearable or mobile device. In these embodiments, the device may enter sleep-tracking mode and monitor a user's sleep without the aid of the charging dock, as will be described in greater detail in connection with FIG. 2. In other embodiments, the systems described herein may be hosted entirely on a charging dock that may enter sleep-tracking mode and monitor a user's sleep without the aid of a device, as will be described in greater detail in connection with FIG. 4. In some embodiments, the systems described herein may be hosted partially on a wearable or mobile device and partially on a charging dock, as will be described in greater detail in connection with FIG. 5. Additionally or alternatively, a charging dock may be designed to facilitate sleep-tracking functionality for a device, as will be described in greater detail in connection with FIGS. 7 and 8.

Figure 2:
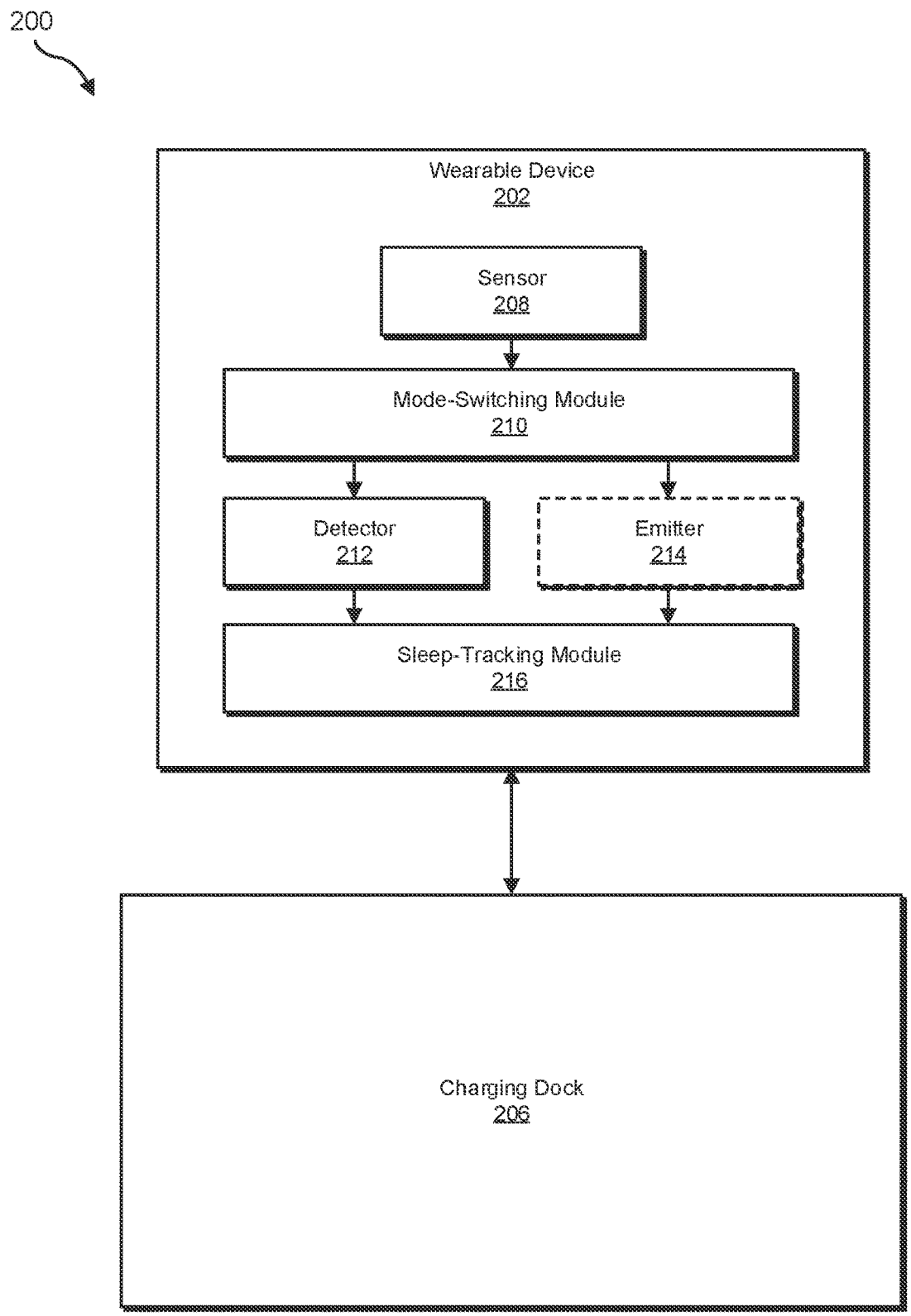
FIG. 2 is a block diagram of an exemplary system for tracking sleep via a wearable device.
Figure 3:
FIG. 3 is a table of an exemplary set of device sensors usable for tracking sleep or performing alternative functions.

FIG. 2 is a block diagram of an exemplary system 200 for sleep tracking that repurposes a wearable device to track the user's sleep while the wearable device is not being worn. In some embodiments, a wearable device 202 may be configured with a sensor 208 that may detect whether the wearable device is being worn by the user. In one embodiment, sensor 208 may detect whether the wearable device is being worn via a biometric sensor, such as a heart rate sensor. In some embodiments, sensor 208 may detect whether the device is being worn based on movement of the device via an accelerometer, gyroscope, inertial measurement unit (IMU), and/or other movement-detecting sensor. In some examples, the systems described herein may infer that the device is not being worn if the device is completely stationary for a period of time (e.g., one minute, five minutes, half an hour, etc.). Additionally or alternatively, sensor 208 may detect whether the device is in physical contact with a charging dock 206 (and therefore highly unlikely to be currently attached to the user's body). In some embodiments, wearable device 202 may be configured with a mode-switching module 210 that switches wearable device 202 between an active mode when sensor 208 detects that the wearable device 202 is being worn by the user and a sleep-tracking mode when sensor 208 detects that wearable device 202 is not being worn by the user.

In some embodiments, wearable device 202 may be configured with a detector 212 that, when wearable device 202 is in the sleep-tracking mode, detects signals associated with sleep behavior of the user. The term "signals associated with sleep behavior" or "signals" may generally refer to any measurable and/or detectable indications of a user's position, movement, and/or state during sleep and/or during attempts to sleep. In some examples, detector 212 may detect a certain category of signals, such as audible signals, visual signals, and/or movement. For example, detector 212 may be a microphone that is used to detect the sound of a user's breathing. In another example, detector 212 may be a camera that is used to visually monitor a user's body position and/or movement during sleep. Additionally or alternatively, detector 212 may be a gyroscope or accelerometer that detects vibrations produced by a user's breathing, heartbeat, and/or movement. In some embodiments, the systems described herein may conserve power by only activating detector 212 when there are relevant signals for detector 212 to capture. For example, the systems described herein may determine, based on an accelerometer, that a user is moving and may then activate a camera to capture more detailed visual data about the user's sleep position. In some examples, the systems described herein may use machine learning to determine when to activate various sensors and/or detectors based on signals detected by other detectors, the current time, the environment, and/or any other relevant factor.

In some embodiments, wearable device 202 may be configured with an emitter 214 that, when wearable device 202 is in sleep-tracking mode, emits radiation toward the user. In these embodiments, the signals associated with the sleep behavior of the user (e.g., that are detected by detector 212) may include radiation reflected off the user. For example, emitter 214 may emit IR light toward the user, enabling an IR camera to detect the user's position based on the IR light reflected off the user. In another example, emitter 214 may emit structured light (e.g., light that forms a pattern, such as bars, a grid, etc.) toward the user. Additionally or alternatively, emitter 214 may emit low levels of visible light (e.g., levels that are low enough not to disturb the user's sleep but bright enough to enable a camera to capture images or video of the user). In one embodiment, emitter 214 may include a light detecting and ranging (LIDAR) emitter. In some embodiments, detector 212 may detect the radiation reflected off the user that is emitted by emitter 214.

In some embodiments, wearable device 202 may be configured with a sleep-tracking module 216 that, when wearable device 202 is in sleep-tracking mode, monitors the user's sleep based at least in part on an evaluation of the signals associated with the sleep behavior of the user. For example, and as will be explained in greater detail below in connection with other figures, sleep-tracking module 216 may monitor a user's sleep cycles, periods of wakefulness, and/or other sleep behaviors or indicators of sleep quality based at least in part on an evaluation of the user's position, movement, breathing, and/or other signals as detected by detector 212 and/or additional detectors. In some examples, sleep-tracking module 216 may perform an evaluation of the signals locally on wearable device 202. In other examples, sleep-tracking module 216 may send data about the signals to a smart device hub and/or remote server for evaluation. In some embodiments, wearable device 202 may be configured with additional detectors and/or sensors that monitor factors that may influence the user's sleep that are not the sleep behavior of the user, such as the temperature of the room, the level of noise in the room, and/or other factors. In these embodiments, sleep-tracking module 216 may evaluate the user's sleep based partially on these additional factors. In some examples, sleep-tracking module 216 may monitor a user's sleep cycles, depth of sleep, periods of wakefulness, and/or other features of sleep based on the signals associated with the sleep behavior.

In some embodiments, wearable device 202 and/or a mobile device may be designed to perform a function unrelated to sleep tracking and the systems described herein may repurpose various sensors of the device to perform sleep-tracking functions. In these embodiments, the various sensors and/or detectors of the device may perform different functions when the device is in active mode as opposed to sleep-tracking mode. For example, as illustrated in table 300 in FIG. 3, when a device is in active mode, a camera may detect a user's location by identifying features of a room (e.g., as part of a pair of artificial reality glasses). However, when the device is in sleep-tracking mode, the camera may detect IR light reflected off the user to monitor the user's movements during sleep. Similarly, a microphone may detect voice commands when a device is in active mode (e.g., as part of a smart clothing item) and may detect breathing patterns when the device is in sleep-tracking mode. In some examples, an accelerometer may assist a navigation app in active mode (e.g., as part of a smart phone) and may detect movement of the bed caused by the user's movements when in sleep-tracking mode. In one example, a gyroscope may detect a user's workout data in active mode (e.g., as part of a smart watch) and may also detect when the device has stopped moving for a period of time and is therefore likely no longer being worn, initiating a transition into sleep-tracking mode. In some embodiments, the wearable device may include at least one hardware element that performs a specified function only when the wearable device is being worn by the user when in the active mode and does not perform any function when the wearable device is in sleep-tracking mode. For example, a wearable device may include a screen that displays data for the user when in active mode but performs no functions in sleep-tracking mode. In another example, a mobile device may include a global positioning system sensor that provides location data to various apps when the mobile device is in active mode but performs no functions in sleep-tracking mode.

Figure 4:
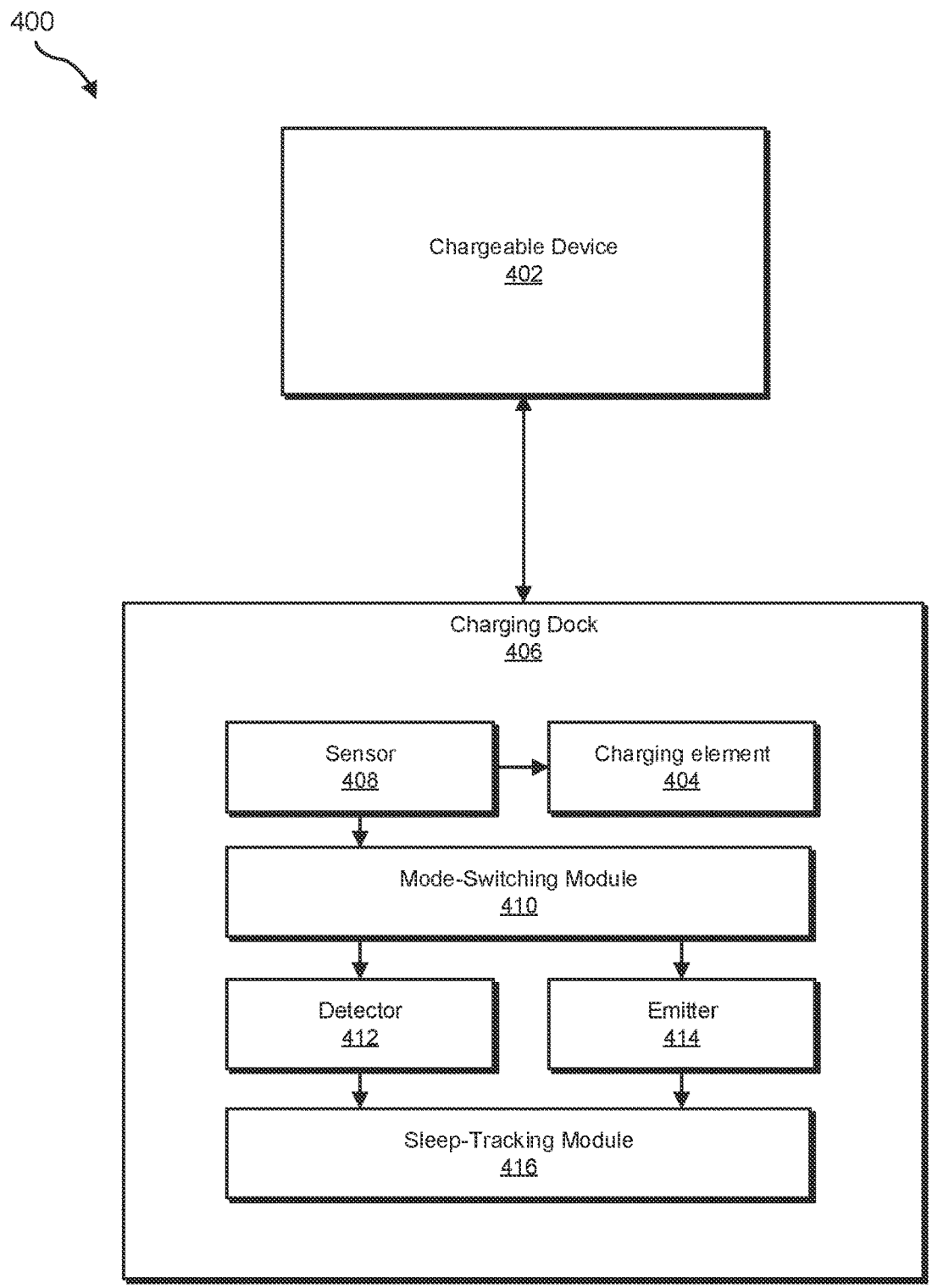
FIG. 4 is a block diagram of an exemplary system for tracking sleep via a charging dock.

In some embodiments, in addition to or as an alternative from repurposing a smart device, the systems described herein may use a device charging dock to perform sleep tracking. For example, as illustrated in FIG. 4, a system 400 for tracking sleep may include a charging dock 406 that charges at least one chargeable device 402. In one embodiment, charging dock 406 may be configured with a sensor 408 that detects whether chargeable device 402 is in physical contact with charging dock 406. For example, sensor 408 may detect whether charging dock 406 is sending charge to chargeable device 402 via a charging element 404, whether chargeable device 402 is resting atop charging dock 406 (e.g., via a weight sensor and/or proximity sensor), whether chargeable device 402 is enclosed within charging dock 406, and/or whether a cable of charging dock 406 is connected to chargeable device 402. In some embodiments, charging dock 406 may be configured with a mode-switching module 410 that switches charging dock 406 between an inactive mode when chargeable device 402 is not in physical contact with charging dock 406 and a sleep-tracking mode when chargeable device 402 is in physical contact with charging dock 406. Additionally, in some examples, charging element 404 may charge chargeable device 402 in response to sensor 408 detecting that chargeable device 402 is in physical contact with charging dock 406.

In some embodiments, charging dock 406 may be configured with an emitter 414 that, when charging dock 406 is in sleep-tracking mode, emits radiation toward a user. For example, emitter 414 may be a visible light emitter, a structured light emitter, an IR emitter, and/or a LIDAR emitter, as discussed above in conjunction with emitter 214 in FIG. 2. In one embodiment, charging dock 406 may be configured with a detector 412 that, when charging dock 406 is in sleep-tracking mode, detects radiation reflected off the user (e.g., after being emitted by emitter 414). In some embodiments, charging dock 406 may be configured with additional sensors and/or detectors, such as a microphone, accelerometer, thermometer, and/or any other suitable sensors for performing sleep-tracking functions. In one embodiment, charging dock 406 may be configured with a sleep-tracking module 416 that, when charging dock 406 is in sleep-tracking mode, monitors the user's sleep based at least in part on an evaluation of the emitted radiation and the detected radiation. For example, sleep-tracking module 416 may identify the user's sleep cycle based on body movement detected via an IR camera (e.g., detector 412). In one embodiment, detector 412 may include a passive IR detector that does not require an IR emitter. In some embodiments, sleep-tracking module 416 may evaluate the sleep signals locally within charging dock 406. Additionally or alternatively, sleep-tracking module 416 may send data to an additional device (e.g., a mobile device), a smart home hub and/or a remote server for evaluation. In some examples, sleep-tracking module 416 may monitor a user's sleep cycles, depth of sleep, periods of wakefulness, and/or other features of sleep based on the signals associated with the sleep behavior.

Figure 5:
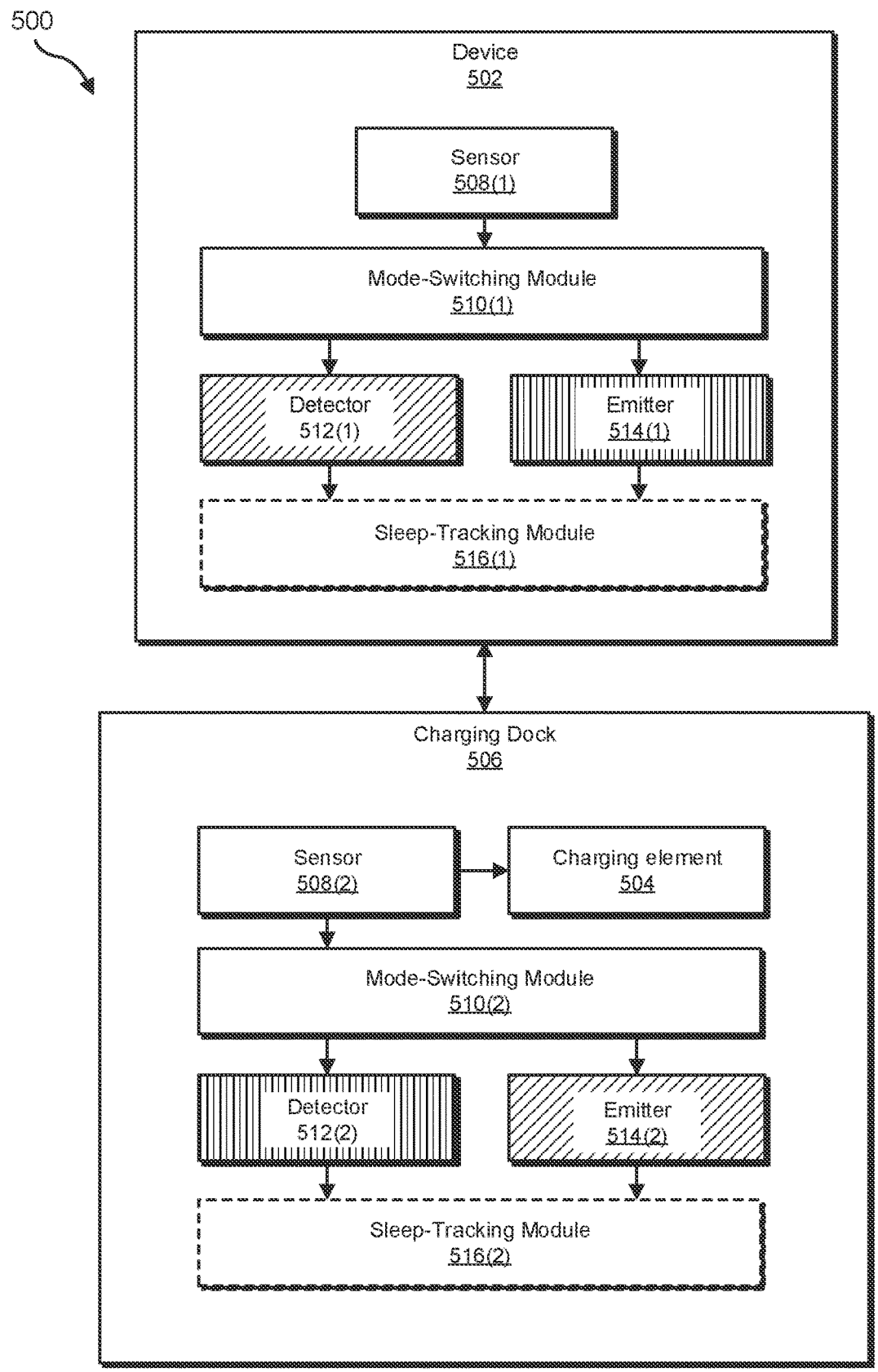
FIG. 5 is a block diagram of an exemplary system for tracking sleep via a device in combination with a charging dock.

In some embodiments, rather than being hosted entirely on a device or entirely on a charging dock, the systems described herein may be hosted on a device and a charging dock functioning in conjunction. For example, as illustrated in FIG. 5, system 500 is a system for tracking sleep via a device 502 and charging dock 506. In some embodiments, a device 502 may be configured with a sensor 508(1) that detects whether device 502 is being worn and/or actively used by the user (e.g., as described above in connection with sensor 208 in FIG. 2) and a mode-switching module 510(1) that switches device 502 between active mode and sleep-tracking mode. Similarly, charging dock 506 may be configured with a sensor 508(2) that detects whether device 502 is in physical contact with charging dock 506 (e.g. as described above in connection with sensor 408 in FIG. 4) and a mode-switching module 510(2) that switches charging dock 506 between inactive mode and sleep-tracking mode. In one embodiment, charging dock 506 may be configured with a charging element 504 that provides charge to device 502 when device 502 is in physical contact with charging dock 506.

In one embodiment, device 502 may be configured with an emitter 514(1) that emits radiation while in sleep-tracking mode and charging dock 506 may be configured with a detector 512(2) that, during sleep-tracking mode, detects radiation emitted by emitter 514(1) and reflected off the user. Additionally or alternatively, charging dock 506 may be configured with an emitter 514(2) that emits radiation while in sleep-tracking mode and device 502 may be configured with a detector 512(1) that, during sleep-tracking mode, detects radiation emitted by emitter 514(2) and reflected off the user. For example, device 502 may be a pair of smart glasses that include a camera that detects light but do not include any kind of light emitter. In this example, charging dock 506 may be configured with a light emitter (e.g., a structured light emitter) that emits light to be detected by the camera of device 502, enabling device 502 to perform sleep-tracking functions with existing sensors without any change to the hardware of device 502.

By configuring charging dock 506 with detectors and/or emitters, the systems described herein may enable a variety of off-the-shelf devices to be repurposed to perform non-intrusive sleep-tracking functions. To further this goal, in some embodiments, charging dock 506 may be dimensioned to hold device 502 such that detector 512(1) faces toward the user during sleep and/or emitter 514(1) faces toward the user during sleep. For example, charging dock 506 may hold a smart phone with the camera facing toward the user during sleep. Additionally or alternatively, device 502 may be dimensioned such that device 502 is physically compatible with charging dock 506 and/or when the device 502 is placed in physical contact with charging dock 506, detector 512(1) and/or emitter 514(1) face toward the user.

In some embodiments, device 502 may be configured with a sleep-tracking module 516(1) that monitors the user's sleep based on an evaluation of signals detected by device 502 and/or charging dock 506, as described in connection with sleep-tracking module 216 in FIG. 2. Additionally or alternatively, charging dock 506 may be configured with a sleep-tracking module 516(2) that monitors the user's sleep based on an evaluation of signals detected by device 502 and/or charging dock 506.

Figure 6:
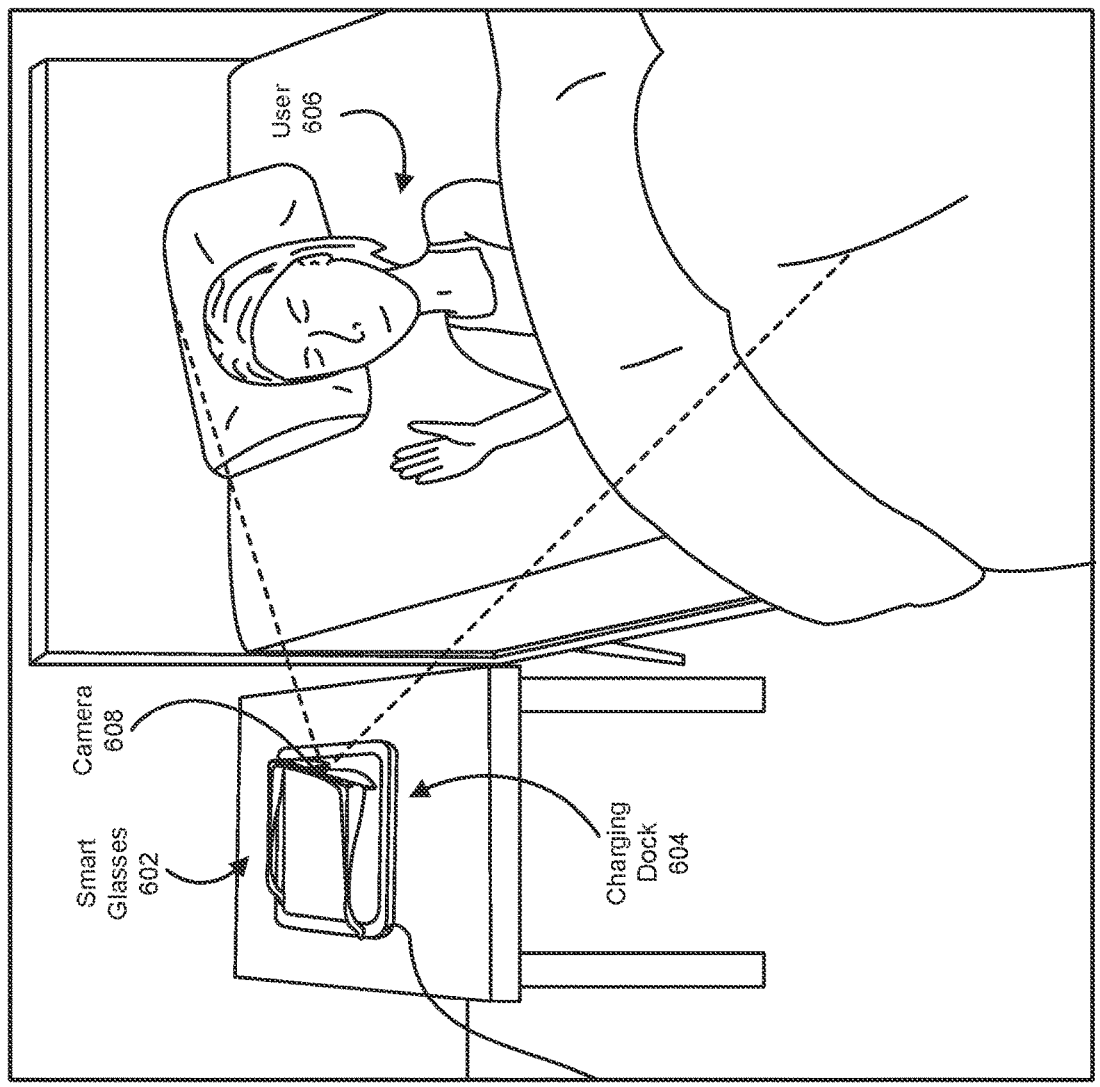
FIG. 6 is an illustration of an exemplary sleep-tracking system that includes smart glasses.

The various embodiments of performing sleep tracking via emitters and/or detectors on some combination of a device and/or a dock may be implemented with a variety of different types of devices and/or docks. For example, the device may be a pair of smart glasses and the charging dock may be a flat dock that charges the smart glasses inductively when the smart glasses are placed on the dock. In one example, as illustrated in FIG. 6, a pair of smart glasses 602 may, when placed on a charging dock 604, receive charge from charging dock 604 and/or enter sleep-tracking mode. In some examples, a camera 608 of smart glasses 602 may monitor a user 606 during sleep. In some embodiments, camera 608 may capture images and/or video of user 606 using ambient light in the room. Additionally or alternatively, smart glasses 602 and/or charging dock 604 may be configured with an emitter (e.g., an IR emitter, structured light emitter, etc.) that emits light toward user 606. In some embodiments, smart glasses 602 and/or charging dock 604 may be configured with additional sensors that detect additional signals associated with the sleep behavior of user 606, such as a microphone, accelerometer, gyroscope, IMU, and/or other relevant sensors.

Figure 7:
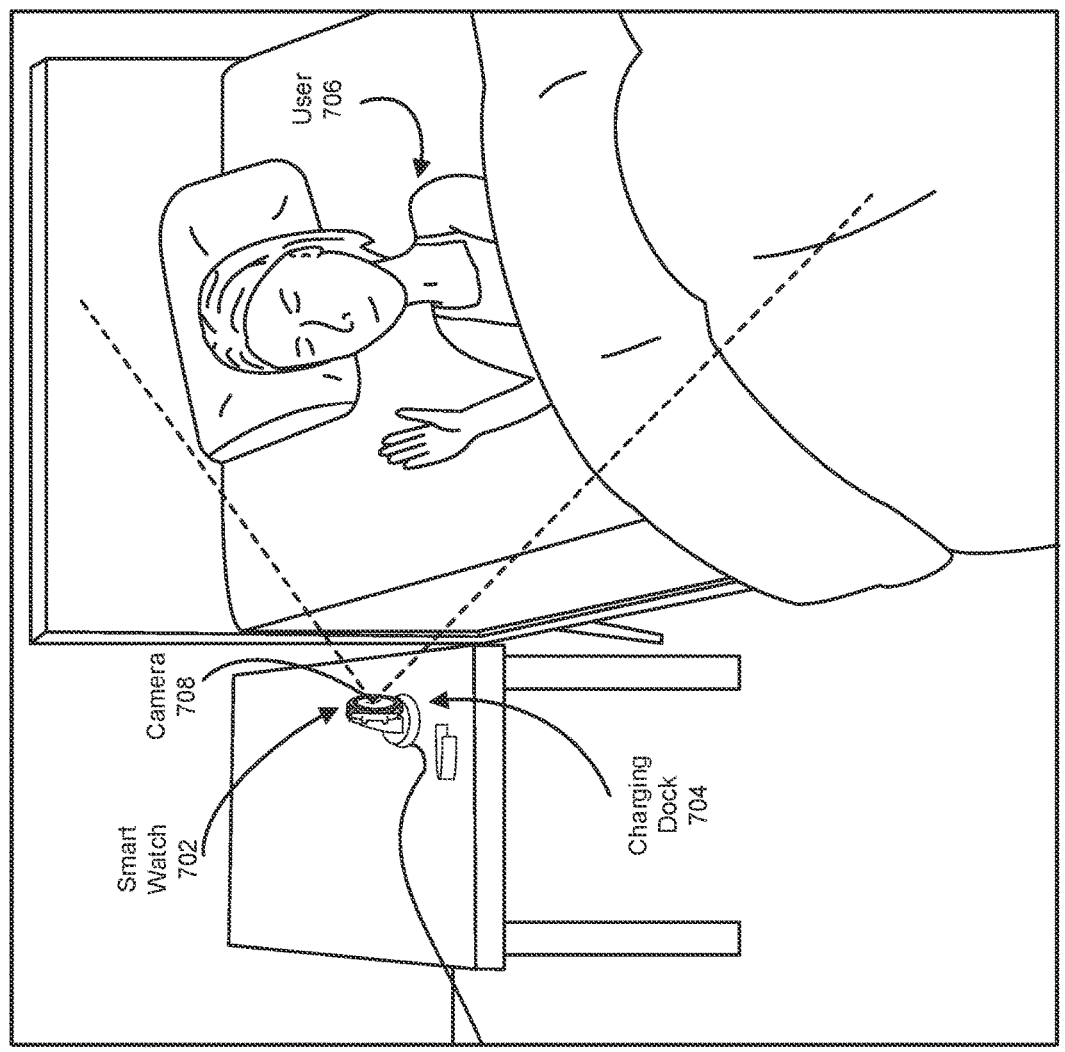
FIG. 7 is an illustration of an exemplary sleep-tracking system that includes a smart watch.

In some embodiments, a charging dock may be shaped to hold a device such that relevant emitters and/or sensors of the device are pointed towards the sleeping user. For example, as illustrated in FIG. 7, a charging dock 704 may be shaped to hold a smart watch 702 such that the face of smart watch 702, which includes a camera 708, is pointed toward a user 706 during sleep. In some embodiments, camera 708 may monitor user 706 during sleep. In one embodiment, the face of smart watch 702 may also contain an emitter, such as an IR emitter, that faces towards user 706 when smart watch 702 is held by charging dock 704.

Figure 8:
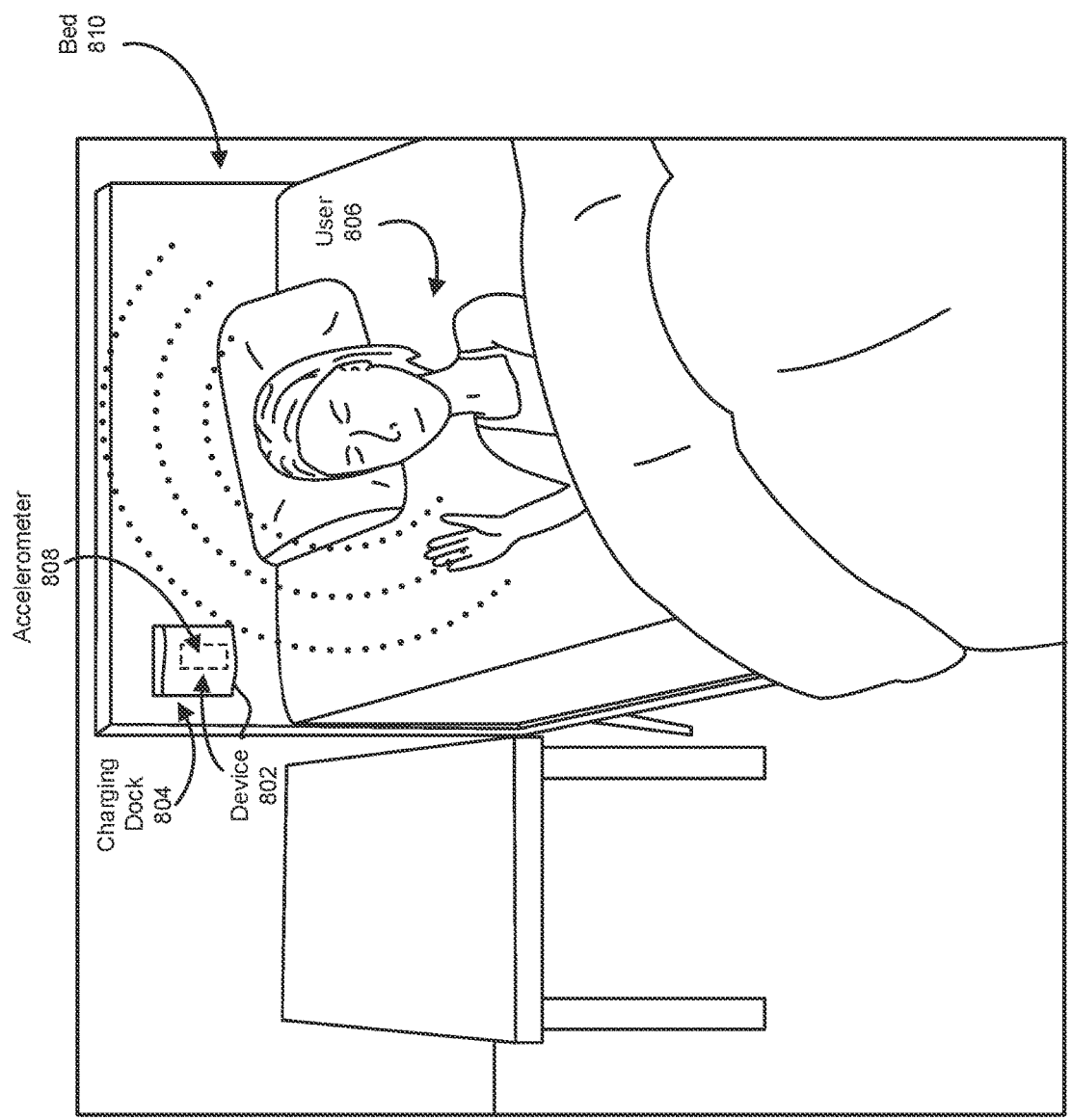
FIG. 8 is an illustration of an exemplary sleep-tracking system that includes a bed-mounted charging dock.

In one embodiment, a charging dock may be affixed to an element of a bed, enabling the charging dock and/or the device to detect vibrations caused by the user and transmitted through the bed. For example, as illustrated in FIG. 8, a charging dock 804 may be affixed to the headboard of a bed 810. In other embodiments, a charging dock may be affixed to the side of a bed, the leg of a bed, a mattress on the bed, and/or any other suitable element of a bed. In some examples, a device 802 placed within charging dock 804 may include an accelerometer 808 that detects vibrations caused by the breathing, heartbeat, and/or movement of user 806 that are transmitted through bed 810 (e.g., through the mattress, headboard, leg, etc.) to charging dock 804. In some examples, accelerometer 808 may be sensitive enough to function as a ballistic cardiograph, detecting the force of the heartbeat of user 806. In one embodiment, charging dock 804 may include a pouch or other housing in which device 802 may be placed. In some embodiments, charging dock 804 may be dimensioned to be affixed to a specific element of a bed (e.g., a headboard or a mattress) while in other embodiments, charging dock 804 may be dimensioned to be affixed to any of a variety of elements of a bed. In some examples, device 802 may be a mobile device, such as a smart phone. In other examples, device 802 may be a wearable device, such as a smart watch, smart glasses, and/or a multi-purpose wearable device capable of being worn in different configurations. In one example, charging dock 804 may inductively charge devices placed within charging dock 804 via an inductive coil.

In some embodiments, the systems described herein may be calibrated to account for different types of beds and/or mattresses to which charging dock 804 may be affixed. For example, a large bed with a thick mattress may transmit vibrations differently than a small bed with a thin mattress. In some examples, the systems described herein may be calibrated to account for the element to which charging dock 804 is affixed (e.g., calibrating differently if charging dock 804 is affixed to a mattress versus a headboard). In some examples, the systems described herein may automatically calibrate via machine learning over a period of time. Additionally or alternatively, the systems described herein may prompt a user to enter data about the type of bed and/or mattress and/or location of charging dock 804 and may calibrate based on the user-provided data.

In some embodiments, the systems described herein may preprocess, process, and/or analyze sleep-tracking data collected from various sensors of the device and/or charging dock in order to evaluate the quality of a user's sleep in ways comparable to a standard sleep study. In some examples, the medical standard for monitoring sleep may involve an electroencephalogram, electrocardiogram, pulse oximetry, and/or respiration monitoring. While not all of this monitoring may be performed non-intrusively by repurposed devices and/or sensors, by monitoring heartbeat (e.g., via vibrations detected by an accelerometer), respiration (e.g., via a microphone), movement (e.g., via a camera and/or accelerometer), posture (e.g., via a camera), and/or environmental conditions of the room (e.g., temperature, ambient noise, light, etc.), and analyzing the resulting data, the systems described herein may perform high-quality analyses of users' sleep that may enable users to identify health problems and/or improve sleep health without the expense of a sleep study and without the discomfort of intrusive sleep-monitoring devices.

The systems described herein may process and/or analyze gathered data to evaluate a user's sleep in a variety of ways. For example, the systems described herein may determine a user's sleep posture by performing feature extraction, feature selection, and classification on visual data from a camera. In another example, the systems described herein may extract and select features from audio data to determine breathing patterns characteristic of different phases of sleep and/or sleep disorders (e.g., sleep apnea, seizures, etc.). In one example, the systems described herein may detect patterns in heartbeat data to calculate a user's heart rate variability. In some embodiments, the systems described herein may analyze collected data (e.g., visual data, audio data, etc.) via machine learning models and/or algorithms, such as a neural network. In some examples, the systems described herein may use data about sleep posture, breathing patterns, heart rate variability, and/or other data generated by analyzing the signals associated with the user's sleep behavior to determine the overall quality of a user's sleep, track a user's sleep cycles and/or sleep disruptions throughout the night, and/or identify health problems. In some embodiments, the systems described herein may use collected data not directly related to the user (e.g., room temperature, ambient noise level, etc.) to provide additional clarity into the user's sleep habits and/or health.

As described above, the systems and methods described herein may repurpose devices with other functions that are already placed on or next to a user's bed during sleep to perform convenient, non-intrusive sleep monitoring. For example, the systems described herein may use the sensors of a wearable device, a mobile device, and/or a charging dock, alone or in combination with one or more other devices, to monitor a user's breathing, heartbeat, body position, and/or other sleep behaviors. In some examples, the device may already be configured with these sensors for non-sleep-tracking purposes, such as a mobile device configured with a microphone to enable the user to make calls or an artificial reality headset configured with cameras to enable an artificial reality system to determine the user's location in a room. In some embodiments, a device may be configured with additional sensors and/or emitters to enable more effective sleep tracking. For example, a charging dock may be configured with a structured light emitter to enable a camera on a device in contact with the charging dock to monitor the position of a user during sleep when the camera would otherwise not be able to capture useful visual data of the user due to the lack of light in the room. By performing sleep tracking non-intrusively using devices the user already owns for other purposes, the systems described herein may enable users to conveniently improve their sleep and therefore their overall physical and mental health.

Embodiments of the present disclosure may include or be implemented in conjunction with various types of artificial reality systems. Artificial reality is a form of reality that has been adjusted in some manner before presentation to a user, which may include, for example, a virtual reality, an augmented reality, a mixed reality, a hybrid reality, or some combination and/or derivative thereof. Artificial-reality content may include completely computer-generated content or computer-generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial-reality systems may be implemented in a variety of different form factors and configurations. Some artificial reality systems may be designed to work without near-eye displays (NEDs). Other artificial reality systems may include an NED that also provides visibility into the real world (such as, e.g., augmented-reality system 900 in FIG. 9) or that visually immerses a user in an artificial reality (such as, e.g., virtual-reality system 1000 in FIG. 10). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 9:
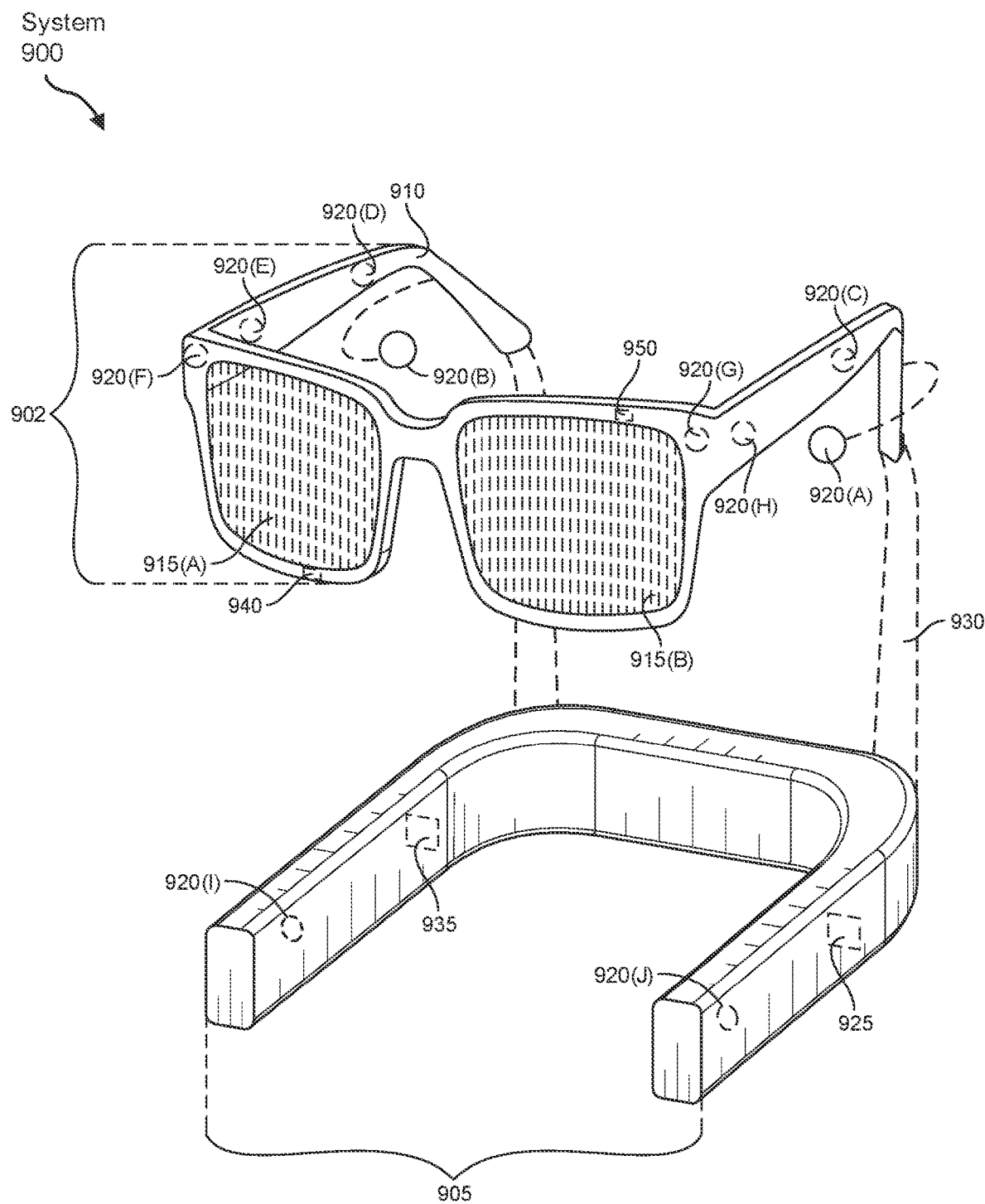
FIG. 9 is an illustration of exemplary augmented-reality glasses that may be used in connection with embodiments of this disclosure.
Figure 10:
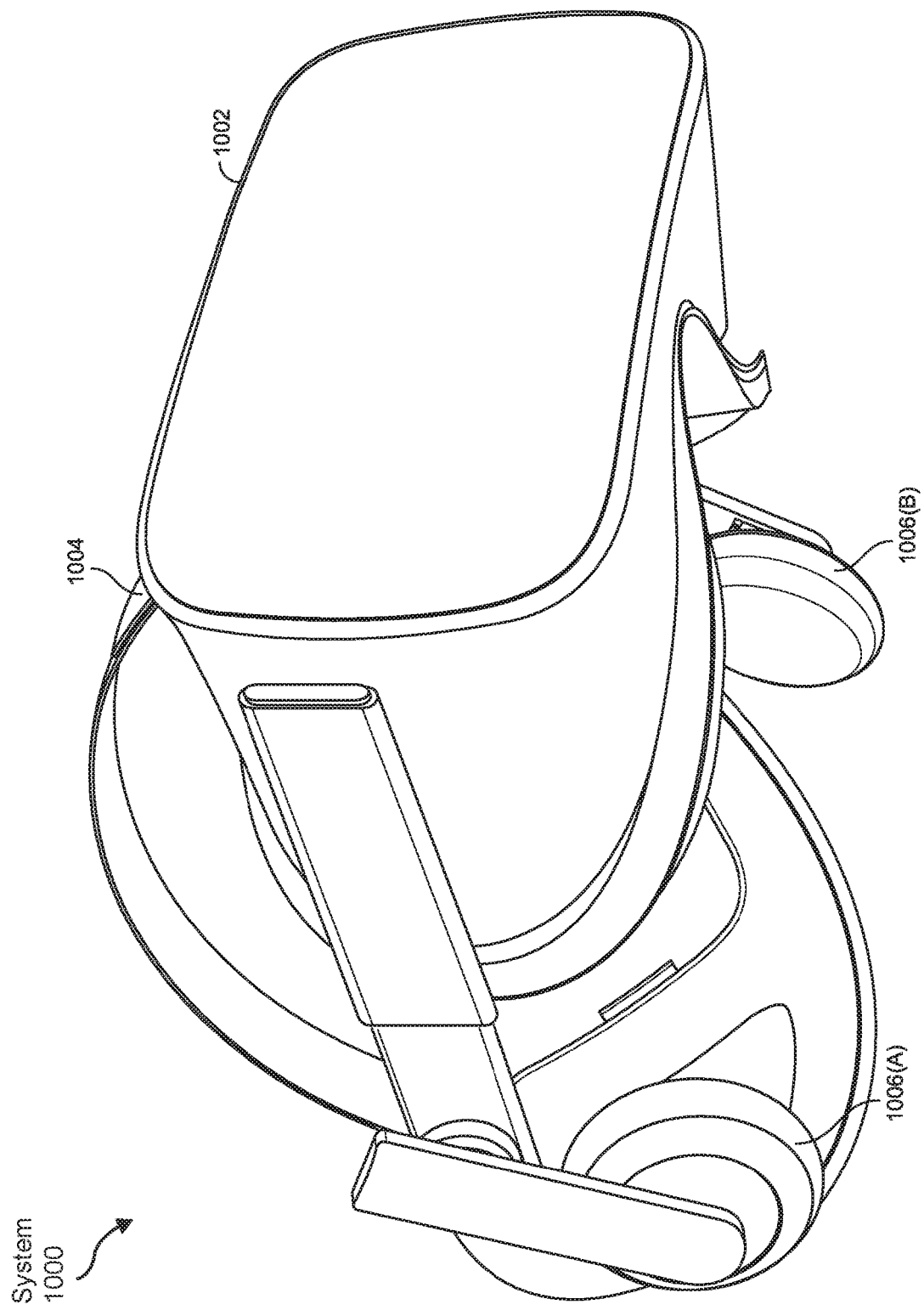
FIG. 10 is an illustration of an exemplary virtual-reality headset that may be used in connection with embodiments of this disclosure.

Turning to FIG. 9, augmented-reality system 900 may include an eyewear device 902 with a frame 910 configured to hold a left display device 915(A) and a right display device 915(B) in front of a user's eyes. Display devices 915(A) and 915(B) may act together or independently to present an image or series of images to a user. While augmented-reality system 900 includes two displays, embodiments of this disclosure may be implemented in augmented-reality systems with a single NED or more than two NEDs.

In some embodiments, augmented-reality system 900 may include one or more sensors, such as sensor 940. Sensor 940 may generate measurement signals in response to motion of augmented-reality system 900 and may be located on substantially any portion of frame 910. Sensor 940 may represent one or more of a variety of different sensing mechanisms, such as a position sensor, an inertial measurement unit (IMU), a depth camera assembly, a structured light emitter and/or detector, or any combination thereof. In some embodiments, augmented-reality system 900 may or may not include sensor 940 or may include more than one sensor. In embodiments in which sensor 940 includes an IMU, the IMU may generate calibration data based on measurement signals from sensor 940. Examples of sensor 940 may include, without limitation, accelerometers, gyroscopes, magnetometers, other suitable types of sensors that detect motion, sensors used for error correction of the IMU, or some combination thereof.

In some examples, augmented-reality system 900 may also include a microphone array with a plurality of acoustic transducers 920(A)-120(J), referred to collectively as acoustic transducers 920. Acoustic transducers 920 may represent transducers that detect air pressure variations induced by sound waves. Each acoustic transducer 920 may be configured to detect sound and convert the detected sound into an electronic format (e.g., an analog or digital format). The microphone array in FIG. 9 may include, for example, ten acoustic transducers: 920(A) and 920(B), which may be designed to be placed inside a corresponding ear of the user, acoustic transducers 920(C), 920(D), 920(E), 920(F), 920 (G), and 920(H), which may be positioned at various locations on frame 910, and/or acoustic transducers 920(1) and 920(J), which may be positioned on a corresponding neckband 905.

In some embodiments, one or more of acoustic transducers 920(A)-(J) may be used as output transducers (e.g., speakers). For example, acoustic transducers 920(A) and/or 920(B) may be earbuds or any other suitable type of headphone or speaker.

The configuration of acoustic transducers 920 of the microphone array may vary. While augmented-reality system 900 is shown in FIG. 9 as having ten acoustic transducers 920, the number of acoustic transducers 920 may be greater or less than ten. In some embodiments, using higher numbers of acoustic transducers 920 may increase the amount of audio information collected and/or the sensitivity and accuracy of the audio information. In contrast, using a lower number of acoustic transducers 920 may decrease the computing power required by an associated controller 950 to process the collected audio information. In addition, the position of each acoustic transducer 920 of the microphone array may vary. For example, the position of an acoustic transducer 920 may include a defined position on the user, a defined coordinate on frame 910, an orientation associated with each acoustic transducer 920, or some combination thereof.

Acoustic transducers 920(A) and 920(B) may be positioned on different parts of the user's ear, such as behind the pinna, behind the tragus, and/or within the auricle or fossa. Or, there may be additional acoustic transducers 920 on or surrounding the ear in addition to acoustic transducers 920 inside the ear canal. Having an acoustic transducer 920 positioned next to an ear canal of a user may enable the microphone array to collect information on how sounds arrive at the ear canal. By positioning at least two of acoustic transducers 920 on either side of a user's head (e.g., as binaural microphones), augmented-reality device 900 may simulate binaural hearing and capture a 3D stereo sound field around about a user's head. In some embodiments, acoustic transducers 920(A) and 920(B) may be connected to augmented-reality system 900 via a wired connection 930, and in other embodiments acoustic transducers 920(A) and 920(B) may be connected to augmented-reality system 900 via a wireless connection (e.g., a BLUETOOTH connection). In still other embodiments, acoustic transducers 920(A) and 920(B) may not be used at all in conjunction with augmented-reality system 900.

Acoustic transducers 920 on frame 910 may be positioned in a variety of different ways, including along the length of the temples, across the bridge, above or below display devices 915(A) and 915(B), or some combination thereof. Acoustic transducers 920 may also be oriented such that the microphone array is able to detect sounds in a wide range of directions surrounding the user wearing the augmented-reality system 900. In some embodiments, an optimization process may be performed during manufacturing of augmented-reality system 900 to determine relative positioning of each acoustic transducer 920 in the microphone array.

In some examples, augmented-reality system 900 may include or be connected to an external device (e.g., a paired device), such as neckband 905. Neckband 905 generally represents any type or form of paired device. Thus, the following discussion of neckband 905 may also apply to various other paired devices, such as charging cases, smart watches, smart phones, wrist bands, other wearable devices, hand-held controllers, tablet computers, laptop computers, other external compute devices, etc.

As shown, neckband 905 may be coupled to eyewear device 902 via one or more connectors. The connectors may be wired or wireless and may include electrical and/or non-electrical (e.g., structural) components. In some cases, eyewear device 902 and neckband 905 may operate independently without any wired or wireless connection between them. While FIG. 9 illustrates the components of eyewear device 902 and neckband 905 in example locations on eyewear device 902 and neckband 905, the components may be located elsewhere and/or distributed differently on eyewear device 902 and/or neckband 905. In some embodiments, the components of eyewear device 902 and neckband 905 may be located on one or more additional peripheral devices paired with eyewear device 902, neckband 905, or some combination thereof.

Pairing external devices, such as neckband 905, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 900 may be provided by a paired device or shared between a paired device and an eyewear device, thus reducing the weight, heat profile, and form factor of the eyewear device overall while still retaining desired functionality. For example, neckband 905 may allow components that would otherwise be included on an eyewear device to be included in neckband 905 since users may tolerate a heavier weight load on their shoulders than they would tolerate on their heads. Neckband 905 may also have a larger surface area over which to diffuse and disperse heat to the ambient environment. Thus, neckband 905 may allow for greater battery and computation capacity than might otherwise have been possible on a stand-alone eyewear device. Since weight carried in neckband 905 may be less invasive to a user than weight carried in eyewear device 902, a user may tolerate wearing a lighter eyewear device and carrying or wearing the paired device for greater lengths of time than a user would tolerate wearing a heavy standalone eyewear device, thereby enabling users to more fully incorporate artificial reality environments into their day-to-day activities.

Neckband 905 may be communicatively coupled with eyewear device 902 and/or to other devices. These other devices may provide certain functions (e.g., tracking, localizing, depth mapping, processing, storage, etc.) to augmented-reality system 900. In the embodiment of FIG. 9, neckband 905 may include two acoustic transducers (e.g., 920(1) and 920(J)) that are part of the microphone array (or potentially form their own microphone subarray). Neckband 905 may also include a controller 925 and a power source 935.

Acoustic transducers 920(1) and 920(J) of neckband 905 may be configured to detect sound and convert the detected sound into an electronic format (analog or digital). In the embodiment of FIG. 9, acoustic transducers 920(1) and 920(J) may be positioned on neckband 905, thereby increasing the distance between the neckband acoustic transducers 920(1) and 920(J) and other acoustic transducers 920 positioned on eyewear device 902. In some cases, increasing the distance between acoustic transducers 920 of the microphone array may improve the accuracy of beamforming performed via the microphone array. For example, if a sound is detected by acoustic transducers 920(C) and 920(D) and the distance between acoustic transducers 920(C) and 920(D) is greater than, e.g., the distance between acoustic transducers 920(D) and 920(E), the determined source location of the detected sound may be more accurate than if the sound had been detected by acoustic transducers 920(D) and 920(E).

Controller 925 of neckband 905 may process information generated by the sensors on neckband 905 and/or augmented-reality system 900. For example, controller 925 may process information from the microphone array that describes sounds detected by the microphone array. For each detected sound, controller 925 may perform a direction-of-arrival (DOA) estimation to estimate a direction from which the detected sound arrived at the microphone array. As the microphone array detects sounds, controller 925 may populate an audio data set with the information. In embodiments in which augmented-reality system 900 includes an inertial measurement unit, controller 925 may compute all inertial and spatial calculations from the IMU located on eyewear device 902. A connector may convey information between augmented-reality system 900 and neckband 905 and between augmented-reality system 900 and controller 925. The information may be in the form of optical data, electrical data, wireless data, or any other transmittable data form. Moving the processing of information generated by augmented-reality system 900 to neckband 905 may reduce weight and heat in eyewear device 902, making it more comfortable to the user.

Power source 935 in neckband 905 may provide power to eyewear device 902 and/or to neckband 905. Power source 935 may include, without limitation, lithium ion batteries, lithium-polymer batteries, primary lithium batteries, alkaline batteries, or any other form of power storage. In some cases, power source 935 may be a wired power source. Including power source 935 on neckband 905 instead of on eyewear device 902 may help better distribute the weight and heat generated by power source 935.

As noted, some artificial reality systems may, instead of blending an artificial reality with actual reality, substantially replace one or more of a user's sensory perceptions of the real world with a virtual experience. One example of this type of system is a head-worn display system, such as virtual-reality system 1000 in FIG. 10, that mostly or completely covers a user's field of view. Virtual-reality system 1000 may include a front rigid body 1002 and a band 1004 shaped to fit around a user's head. Virtual-reality system 1000 may also include output audio transducers 1006(A) and 1006(B). Furthermore, while not shown in FIG. 10, front rigid body 1002 may include one or more electronic elements, including one or more electronic displays, one or more inertial measurement units (IMUS), one or more tracking emitters or detectors, and/or any other suitable device or system for creating an artificial-reality experience.

Artificial reality systems may include a variety of types of visual feedback mechanisms. For example, display devices in augmented-reality system 900 and/or virtual-reality system 1000 may include one or more liquid crystal displays (LCDs), light emitting diode (LED) displays, microLED displays, organic LED (OLED) displays, digital light project (DLP) micro-displays, liquid crystal on silicon (LCoS) micro-displays, and/or any other suitable type of display screen. These artificial reality systems may include a single display screen for both eyes or may provide a display screen for each eye, which may allow for additional flexibility for varifocal adjustments or for correcting a user's refractive error. Some of these artificial reality systems may also include optical subsystems having one or more lenses (e.g., conventional concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some of the artificial reality systems described herein may include one or more projection systems. For example, display devices in augmented-reality system 900 and/or virtual-reality system 1000 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial reality systems may also be configured with any other suitable type or form of image projection system, such as retinal projectors used in virtual retina displays.

The artificial reality systems described herein may also include various types of computer vision components and subsystems. For example, augmented-reality system 900 and/or virtual-reality system 1000 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial reality system may process data from one or more of these sensors to identify a location of a user, to map the real world, to provide a user with context about real-world surroundings, and/or to perform a variety of other functions.

The artificial reality systems described herein may also include one or more input and/or output audio transducers. Output audio transducers may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

In some embodiments, the artificial reality systems described herein may also include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial reality devices, within other artificial reality devices, and/or in conjunction with other artificial reality devices.

By providing haptic sensations, audible content, and/or visual content, artificial reality systems may create an entire virtual experience or enhance a user's real-world experience in a variety of contexts and environments. For instance, artificial reality systems may assist or extend a user's perception, memory, or cognition within a particular environment. Some systems may enhance a user's interactions with other people in the real world or may enable more immersive interactions with other people in a virtual world. Artificial reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial reality experience in one or more of these contexts and environments and/or in other contexts and environments.

Figure 11A:
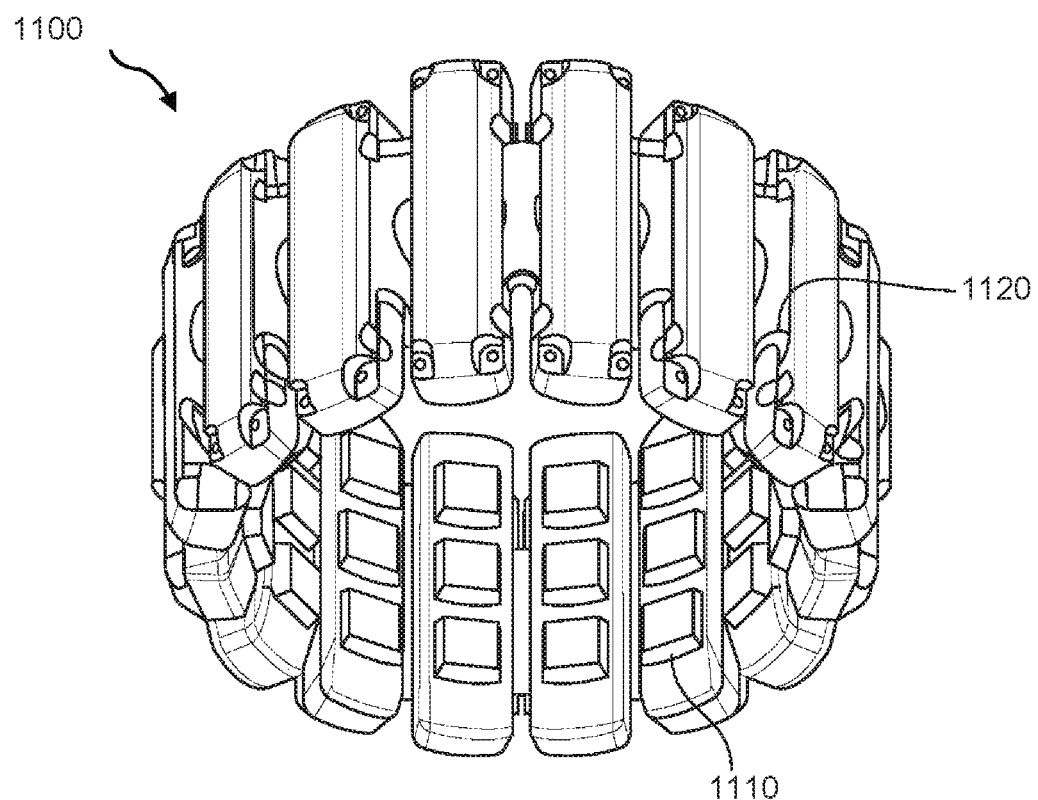
FIGS. 11A and 11B are illustrations of an exemplary human-machine interface configured to be worn around a user's lower arm or wrist.
Figure 11B:
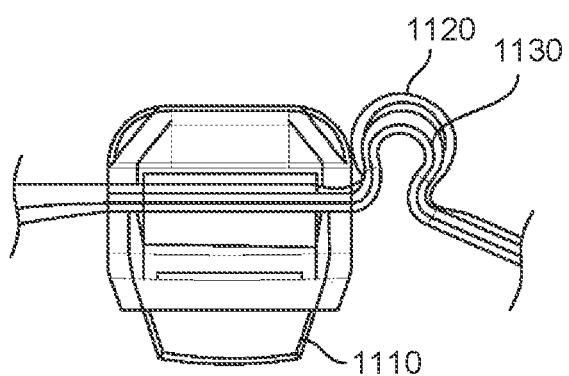

FIG. 11A illustrates an exemplary human-machine interface (also referred to herein as an EMG control interface) configured to be worn around a user's lower arm or wrist as a wearable system 1100. In this example, wearable system 1100 may include sixteen neuromuscular sensors 1110 (e.g., EMG sensors) arranged circumferentially around an elastic band 1120 with an interior surface 1130 configured to contact a user's skin. However, any suitable number of neuromuscular sensors may be used. The number and arrangement of neuromuscular sensors may depend on the particular application for which the wearable device is used. For example, a wearable armband or wristband can be used to generate control information for controlling an augmented reality system, a robot, controlling a vehicle, scrolling through text, controlling a virtual avatar, or any other suitable control task. As shown, the sensors may be coupled together using flexible electronics incorporated into the wireless device. FIG. 11B illustrates a cross-sectional view through one of the sensors of the wearable device shown in FIG. 11A. In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect.

EXAMPLE EMBODIMENTS

Example 1: A wearable device may include (i) a sensor that detects whether a wearable device is being worn by a user, (ii) a mode-switching module that switches the wearable device between an active mode when the sensor detects that the wearable device is being worn by the user and a sleep-tracking mode when the sensor detects that the wearable device is not being worn by the user, (iii) a detector that, when the wearable device is in the sleep-tracking mode, detects signals associated with sleep behavior of the user, and (iv) a sleep-tracking module that, when the wearable device is in the sleep-tracking mode, monitors the user's sleep based at least in part on an evaluation of the signals associated with the sleep behavior of the user.

Example 2: The wearable device of example 1 may further include a housing dimensioned to be physically worn by the user.

Example 3: The wearable device of examples 1-2 may further include an emitter that, when the wearable device is in the sleep-tracking mode, emits radiation toward the user, where the signals associated with the sleep behavior of the user include radiation reflected off the user.

Example 4: The wearable device of examples 1-3, where the emitter includes at least one of an infrared emitter, a visible light emitter, a light detecting and ranging emitter, or a structured light emitter and the detector includes at least one of an infrared detector, a visible light detector, a light detecting and ranging detector, or a structured light detector.

Example 5: The wearable device of examples 1-4, where the signals associated with the sleep behavior of the user include vibrations caused by at least one of the user's breathing, heartbeat, or movement.

Example 6: The wearable device of examples 1-5, may further include a hardware element that performs a specified function only when the wearable device is being worn by the user when in the active mode.

Example 7: The wearable device of examples 1-6, where the detector that detects the signals when the wearable device is in the sleep-tracking mode performs at least one additional function when the wearable device is in the active mode.

Example 8: The wearable device of examples 1-7, where the sensor that detects whether the wearable device is being worn by the user performs at least one additional function when the wearable device is in the active mode.

Example 9: The wearable device of examples 1-8, where the sensor detects whether the wearable device is being worn by the user by detecting whether the wearable device is in physical contact with a charging dock.

Example 10: The wearable device of examples 1-9, where the sensor that detects whether the wearable device is being worn by the user includes at least one of a gyroscope, an accelerometer, or a biometric sensor.

Example 11: The wearable device of examples 1-10, where the wearable device is dimensioned such that the wearable device is physically compatible with a charging dock that is removably attachable to at least a portion of a bed element and/or when the wearable device is placed in physical contact with the charging dock, the detector faces toward the user.

Example 12: A charging dock may include (i) a sensor that detects whether a chargeable device is in physical contact with the charging dock, (ii) a mode-switching module that switches the charging dock between an inactive mode when the chargeable device is not in physical contact with the charging dock and a sleep-tracking mode when the chargeable device is in physical contact with the charging dock, (iii) a charging element that charges the chargeable device in response to the sensor detecting that the chargeable device is in physical contact with the charging dock, (iv) an emitter that, when the charging dock is in the sleep-tracking mode, emits radiation toward a user, (v) a detector that, when the charging dock is in the sleep-tracking mode, detects radiation reflected off the user, and (vi) a sleep-tracking module that, when the charging dock is in the sleep-tracking mode, monitors the user's sleep based at least in part on an evaluation of the emitted radiation and the detected radiation.

Example 13: The wearable device of example 12, where the emitter includes at least one of an infrared emitter, a visible light emitter, a light detecting and ranging emitter, or a structured light emitter and the detector includes at least one of an infrared detector, a visible light detector, a light detecting and ranging detector, or a structured light detector.

Example 14: A system for sleep tracking may include (i) a wearable device, (ii) a charging dock that includes a charging element that charges the wearable device when the wearable device is in physical contact with the charging dock, (iii) a detector that detects signals associated with sleep behavior of a user during a sleep-tracking mode, (iv) a mode-switching module that switches the detector into the sleep-tracking mode when the wearable device is in physical contact with the charging dock, and (v) a sleep-tracking module that monitors the user's sleep based at least in part on an evaluation of the signals associated with the sleep behavior of the user.

Example 15: The system of example 14 may further include an emitter that is housed within at least one of the wearable device or the charging dock.

Example 16: The system of examples 14-16, where the detector is housed within at least one of the wearable device or the charging dock.

Example 17: The system of examples 14-16, where the wearable device further includes a sensor that detects whether the wearable device is being worn by the user and the mode-switching module switches the wearable device between an active mode when the sensor detects that the wearable device is being worn by the user and the sleep-tracking mode when the sensor detects that the wearable device is not being worn by the user.

Example 18: The system of examples 14-17, where the charging dock further includes a sensor that detects whether the wearable device is in physical contact with the charging dock and the mode-switching module switches the charging dock between an inactive mode when the wearable device is not in physical contact with the charging dock and the sleep-tracking mode when the wearable device is in physical contact with the charging dock.

Example 19: The system of examples 14-18, where the charging dock is dimensioned to hold the wearable device such that the detector faces toward the user during sleep and/or an emitter housed within the wearable device faces toward the user during sleep.

Example 20: The system of examples 14-19, where the charging dock is dimensioned to be attached to at least a portion of a bed element and the signals include vibrations transmitted through the bed element to the charging dock.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive image data to be transformed, transform the image data into a data structure that stores user characteristic data, output a result of the transformation to select a customized interactive ice breaker widget relevant to the user, use the result of the transformation to present the widget to the user, and store the result of the transformation to create a record of the presented widget. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A wearable device comprising:
    a housing that is dimensioned to be physically worn by a user;
    a sensor that is configured to detect whether the housing is being worn by the user;
    a mode-switching module that is configured to switch one or more components of the wearable device between an active mode that is used when the sensor detects that the housing is being worn by the user and a sleep-tracking mode that is used when the sensor detects that the housing is not being worn by the user;
    wherein the one or more components comprise a detector that is configured to, when the wearable device is in the sleep-tracking mode, detect signals associated with sleep behavior of the user; and
    a sleep-tracking module that is configured to, when in the sleep-tracking mode, monitor the user's sleep based at least in part on an evaluation of the signals associated with the sleep behavior of the user.

2. The wearable device of claim 1, wherein the one or more components comprise an emitter that, when in the sleep-tracking mode, emits radiation toward the user, wherein the signals associated with the sleep behavior of the user comprise radiation reflected off the user.

3. The wearable device of claim 2, wherein:
    the emitter comprises at least one of:
        an infrared emitter;
        a visible light emitter;
        a light detecting and ranging emitter; or
        a structured light emitter; and
    the detector comprises at least one of:
        an infrared detector;
        a visible light detector;
        a light detecting and ranging detector; or
        a structured light detector.

4. The wearable device of claim 1, wherein the signals associated with the sleep behavior of the user comprise vibrations caused by at least one of the user's:
    breathing;
    heartbeat; or
    movement.

5. The wearable device of claim 1, further comprising a hardware element that performs a specified function only when the hardware element is in the active mode.

6. The wearable device of claim 1, wherein the detector that detects the signals when the wearable device is in the sleep-tracking mode performs at least one additional function when the component that comprises the detector is in the active mode.

7. The wearable device of claim 1, wherein the sensor that detects whether the wearable device is being worn by the user performs at least one additional function when the component that comprises the sensor is in the active mode.

8. The wearable device of claim 1, wherein the sensor detects whether the wearable device is being worn by the user by detecting whether the wearable device is in physical contact with a charging dock.

9. The wearable device of claim 1, wherein the sensor that detects whether the wearable device is being worn by the user comprises at least one of:
    a gyroscope;
    an accelerometer; or
    a biometric sensor.

10. The wearable device of claim 1, wherein the housing of the wearable device is dimensioned such that at least one of:
    the wearable device is physically compatible with a charging dock that is removably attachable to at least a portion of a bed element; or
    when the wearable device is placed in physical contact with the charging dock, the detector faces toward the user.

11. A charging dock comprising:
    a sensor that is configured to detect whether a chargeable device is in physical contact with the charging dock, the chargeable device comprising one or more components configured to, when in a sleep-tracking mode, detect signals associated with sleep behavior of the user;
    a mode-switching module that is configured to switch one or more of the one or more components of the chargeable device between an active mode when the chargeable device is not in physical contact with the charging dock and the sleep-tracking mode when the chargeable device is in physical contact with the charging dock;
    a charging element that is configured to charge the chargeable device in response to the sensor detecting that the chargeable device is in physical contact with the charging dock;
    wherein the one or more components comprise an emitter that is configured to, when in the sleep-tracking mode, emit radiation toward a user;
    wherein the one or more components comprise a detector that is configured to, when in the sleep-tracking mode, detect radiation reflected off the user; and
    wherein the one or more components comprise a sleep-tracking module that is configured to, in the sleep-tracking mode, monitor the user's sleep based at least in part on an evaluation of the emitted radiation and the detected radiation.

12. The charging dock of claim 11, wherein:
    the emitter comprises at least one of:
        an infrared emitter;
        a visible light emitter;
        a light detecting and ranging emitter; or
        a structured light emitter; and
    the detector comprises at least one of:

an infrared detector;
a visible light detector;
a light detecting and ranging detector; or
a structured light detector.

13. A system comprising:
a wearable device;
a charging dock; and
a sleep tracking module;
wherein the wearable device comprises:
   one or more components, the one or more components comprising a detector that is configured to detect signals associated with sleep behavior of a user during a sleep-tracking mode;
   a housing that is dimensioned to be physically worn by a user; and
   a mode-switching module that is configured to switch the one or more components of the wearable device into the sleep-tracking mode when the wearable device is in physical contact with the charging dock;
wherein the charging dock comprises a charging element that is configured to charge the wearable device when the wearable device is in physical contact with the charging dock;
wherein the sleep-tracking module is configured to monitor the user's sleep based at least in part on an evaluation of the signals associated with the sleep behavior of the user.

14. The system of claim 13, further comprising an emitter that is housed within at least one of:
the wearable device; or
the charging dock.

15. The system of claim 13, further comprising an additional detector that is housed within the charging dock.

16. The system of claim 13, wherein:
the wearable device further comprises a sensor that is configured to detect whether the housing is being worn by the user; and
the mode-switching module is configured to switch the one or more components of the wearable device between an active mode when the sensor detects that the housing is being worn by the user and the sleep-tracking mode when the sensor detects that the housing is not being worn by the user.

17. The system of claim 13, wherein:
the charging dock further comprises a sensor that is configured to detect whether the wearable device is in physical contact with the charging dock; and
the mode-switching module is configured to switch one or more components of the charging dock between an inactive mode when the wearable device is not in physical contact with the charging dock and the sleep-tracking mode when the wearable device is in physical contact with the charging dock.

18. The system of claim 13, wherein the charging dock is dimensioned to hold the wearable device such that least one of:
the detector faces toward the user during sleep; or
an emitter housed within the wearable device faces toward the user during sleep.

19. The system of claim 13, wherein:
the charging dock is dimensioned to be attached to at least a portion of a bed element; and
the signals comprise vibrations transmitted through the bed element to the charging dock.

* * * * *